US00PP32056P2

(12) United States Plant Patent
Renault

(10) Patent No.: US PP32,056 P2
(45) Date of Patent: Aug. 11, 2020

(54) ***HYDRANGEA* PLANT NAMED 'RENSAM'**

(50) Latin Name: *Hydrangea paniculata*
Varietal Denomination: RENSAM

(71) Applicant: Jean Renault, Gorron (FR)

(72) Inventor: Jean Renault, Gorron (FR)

( * ) Notice: Subject to any disclaimer, the term of this patent is extended or adjusted under 35 U.S.C. 154(b) by 0 days.

(21) Appl. No.: 16/501,308

(22) Filed: Mar. 22, 2019

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48
See application file for complete search history.

(56) References Cited

PUBLICATIONS

UPOV Plant Breeders' Right QZ PBR 20172032, published Dec. 16, 2017.*

* cited by examiner

*Primary Examiner* — Anne Marie Grunberg
(74) *Attorney, Agent, or Firm* — Cassandra Bright

(57) ABSTRACT

A new and distinct cultivar of *Hydrangea* plant named 'RENSAM' is disclosed, characterized by abundant pyramidal inflorescences on compact plants. Flowers begin white and turn deep pink with maturity. The new variety is a *Hydrangea*, normally produced as an ornamental plant for containers or gardens.

3 Drawing Sheets

Latin name of the genus and species: *Hydrangea paniculata.*

Variety denomination: 'RENSAM'.

BACKGROUND OF THE INVENTION

The new *Hydrangea* cultivar is a product of a planned breeding program conducted by the inventor, Jean Renault in Gorron, France. The objective of the breeding program was to produce new *Hydrangea paniculata* varieties for garden use. The cross pollination resulting in this new variety was made during 2004.

The seed parent is an unnamed, unpatented proprietary variety of *Hydrangea paniculata*. The pollen parent is a different unnamed, unpatented proprietary variety of *Hydrangea paniculata*. The new variety was identified as a potentially interesting selection June of 2007, at a commercial nursery in Gorron, France.

Asexual reproduction of the new cultivar 'RENSAM' by softwood cuttings was first performed in July of 2007, at commercial greenhouse in Gorron, France. Subsequent propagation has shown that the unique features of this cultivar are stable and reproduced true to type in multiple successive generations.

SUMMARY OF THE INVENTION

The cultivar 'RENSAM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RENSAM' These characteristics in combination distinguish 'RENSAM' as a new and distinct *Hydrangea* cultivar:

1. Compact plant habit.
2. Abundant pyramidal inflorescences.
3. Cold hardy to USDA Zone 4.
4. Continuous blooming from July to October in Garron, France.
5. Blooms emerge white, turning deep pink.

PARENT COMPARISON

Plants of the new cultivar 'RENSAM' are similar to plants of seed parent, in most horticultural characteristics, however, plants of the new cultivar 'RENSAM' differ in the following:

1. The new variety produces a smaller inflorescence.
2. The new variety produces deep pink flowers, the seed parent produces lighter colored lavender to pink flowers.

Plants of the new cultivar 'RENSAM' are similar to plants of pollen parent, in most horticultural characteristics, however, plants of the new cultivar 'RENSAM' differ in the following:

1. Plants of the new variety produce more branches, forming a more compact, dense plant.
2. The new variety begins flowering earlier.

COMMERCIAL COMPARISON

'RENSAM' can be compared to the patented commercial variety *Hydrangea paniculata* 'RENHY' U.S. Plant Pat. No. 20,670. These varieties are similar in most horticultural characteristics; however 'RENSAM' differs in the following:

1. The comparator has a larger inflorescence.
2. Plants of the new variety are smaller and more compact.

'RENSAM' can be compared to the patented commercial variety *Hydrangea paniculata* 'Rensun', U.S. Plant Pat. No. 25,438. These varieties are similar in most horticultural characteristics; however 'RENSAM' differs in the following:

1. The comparator produces flowers which begin white, then turn pink, the new variety produces flowers which begin white then turn deep pink.

'RENSAM' can be compared to the patented commercial variety *Hydrangea paniculata* 'RENBA', U.S. Plant Pat. No. 28,509. These varieties are similar in most horticultural characteristics; however 'RENSAM' differs in the following:

1. The comparator has a larger inflorescence.

BRIEF DESCRIPTION OF THE PHOTOGRAPHS

The accompanying photograph in FIG. 1 illustrates in full color a typical plant of 'RENSAM" grown in a 3 gallon pot, in Gorron, France, USA. Age of the plant photographed is approximately 3 years.

Figure 1:
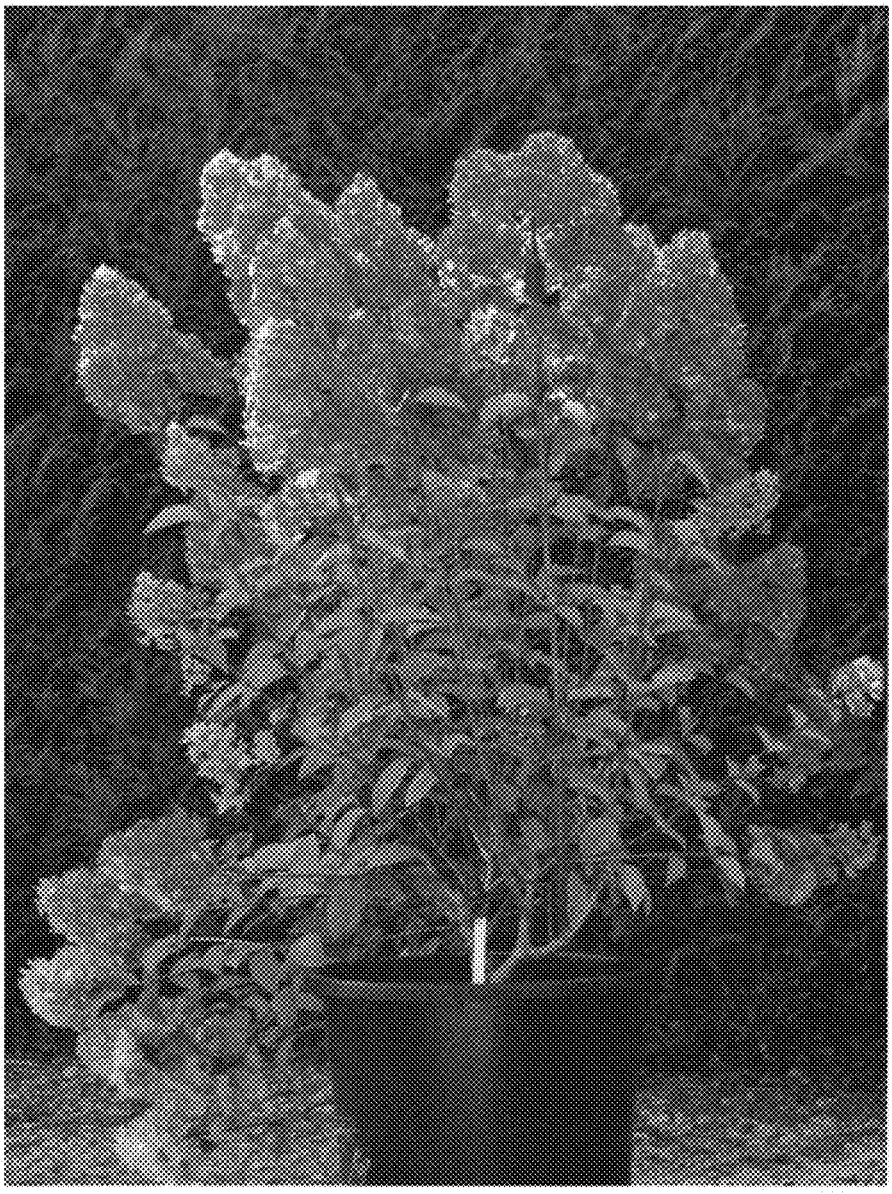
Figure 2:
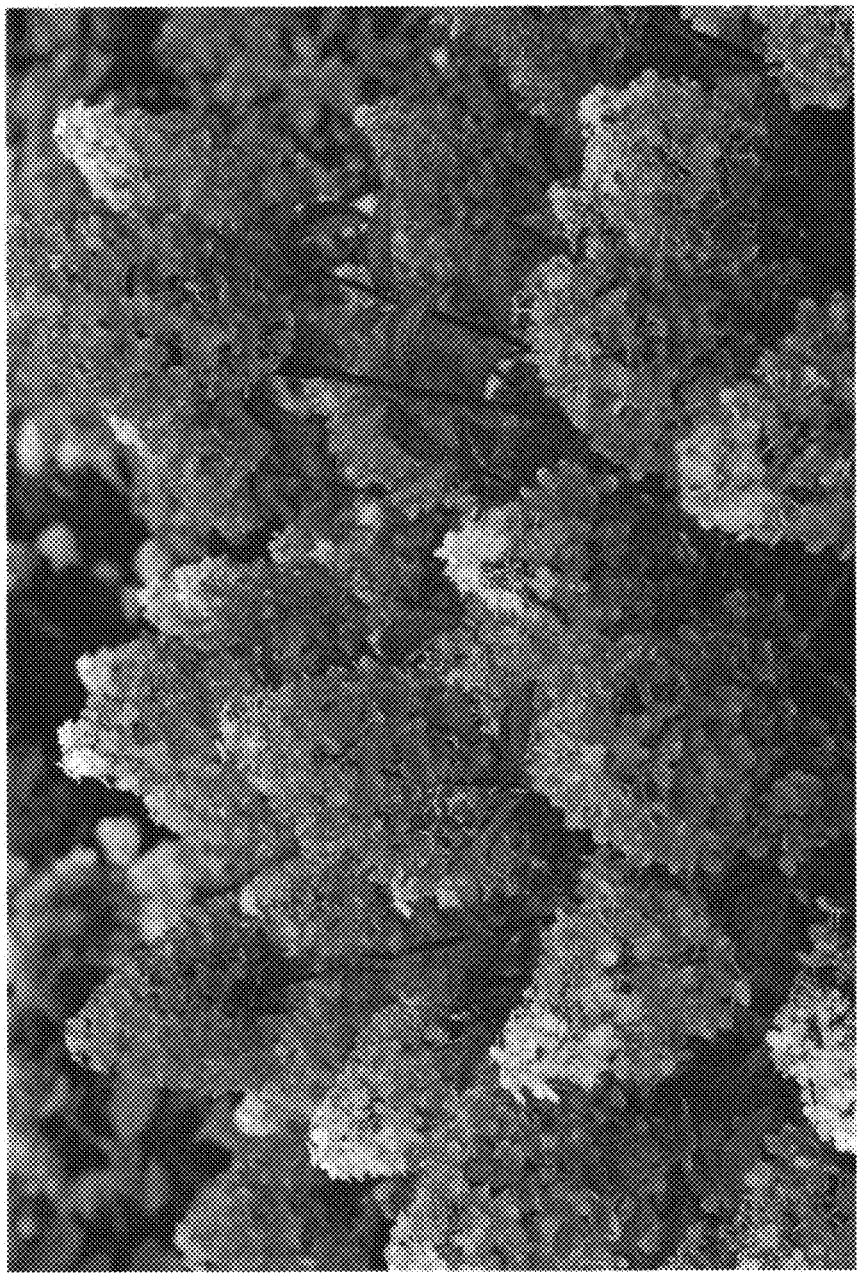
FIG. 2 illustrates typical foliage and inflorescence of the new variety.
Figure 3:
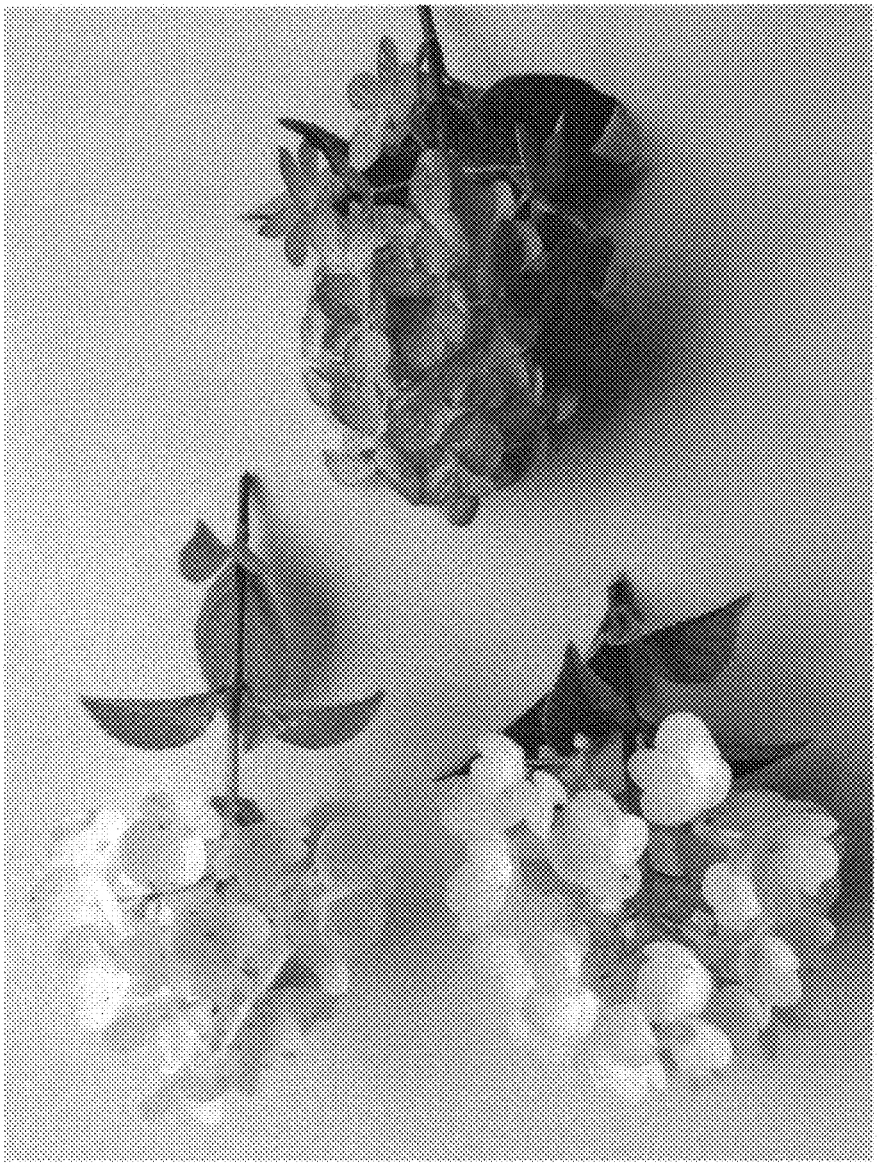
FIG. 3 illustrates the color progression of the flowers, the white flowers are the newly emerged blooms, the deep pink flowers on the right of the photo are the mature flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 2015 Royal Horticultural Society Colour Chart except where general terms of ordinary dictionary significance are used. The following observations and measurements describe 'RENSAM' plants grown in a field, in Gorron, France, USA. The growing temperature ranged from approximately 18° C. to 27° C. daytime and 5° to 10° C. at night. Measurements and numerical values represent averages of typical plant types. Measurements were taken during July of 2018.

Botanical classification: *Hydrangea paniculata* 'RENSAM.'.

PROPAGATION

Time to initiate roots: Approximately 18 days at approximately 24° C.

Time to produce a rooted young plants: Approximately 60 days at approximately 24° C.

Root description: Thin to thick, moderate to dense, freely root branching, fleshy. Color is white and brown. Not accurately measured with a color chart.

Propagation method: Softwood cuttings.

PLANT

Age of plant described: About 2 to 3 years.

Pot size: 3 gallon.

Growth habit: Flowering perennial shrub, or sub-shrub.

Overall plant shape: Upright.

Height: 100 cm.

Plant spread: 70 cm.

Growth rate: Moderate.

Plant vigor: Good.

Branching characteristics: Upright/outward basal branches, some pinching required.

Length of lateral branches: 70 to 90 cm.

Number of lateral branches: 10 to 15.

Diameter of lateral branches: 6 to 8 mm.

Lateral branch shape: Rounded.

Lateral branch strength: Good.

Internode length: Average range 3 to 5 cm.

Branch color: Immature: Near RHS Yellow-Green 146C. Mature: Near RHS Yellow-Green 146C.

Branch aspect: Straight and upright.

Branch texture: Pubescent when young, becoming glabrous with age.

FOLIAGE

Leaf:

- *Arrangement.*—Opposite.
- *Average length.*—10 cm.
- *Average width.*—5 cm.
- *Shape of blade.*—Elliptic.
- *Apex.*—Acuminate.
- *Base.*—Obtuse.
- *Margin.*—Serrate to crenate.
- *Texture and appearance of top surface.*—Rugose, leathery.
- *Texture and appearance of bottom surface.*—Leathery, prominent veins.
- *Leaf pubescence.*—Occurs on upper and lower surfaces, sparse along veins.
- *Color.*—Young foliage upper side: Near RHS Green 138A. Young foliage under side: Near RHS Green 138C. Mature foliage upper side: Near RHS Green 137A. Mature foliage under side: Near RHS Green 137D.
- *Venation.*—Type: Pinnate. Venation color upper side: Near RHS Green 138B. Venation color under side: Near Yellow-Green 1444B.

Petiole:

- *Average length.*—1.8 cm.
- *Diameter.*—3.5 mm.
- *Color.*—Upper side: Near RHS Yellow-green 144A flushed Greyed-Purple 183B.
- *Under side.*—Near RHS Yellow-green 144A.
- *Texture upper side.*—Smooth.
- *Texture under side.*—Smooth.

FLOWER

Bloom period:

- *Natural season.*—Mid-Summer through Fall in Garron, France.

Inflorescence:

- *Type.*—Pyramidal panicles of sterile flowers.
- *Quantity of flowers per inflorescence.*—About 200.
- *Persistent or self-cleaning.*—Persistent.
- *Fragrance.*—None.

Panicle:

- *Shape.*—Pyramidal.
- *Length.*—12.5 cm.
- *Diameter.*—9 cm.

Sterile flower:

- *Bud shape.*—Orbicular and lobed.
- *Bud length.*—3 mm.
- *Bud diameter.*—3 mm.

*Bud color*.—Near RHS Green-White 157A.
*Flower aspect*.—Outward.
*Flower shape*.—Irregularly round.
*Flower diameter*.—Average 3 cm.
*Flower depth*.—1 cm.

Sterile flower sepal:
*Petal arrangement*.—Whorled, partially overlapping.
*Length of petal*.—3.2 mm.
*Width of petal*.—2.8 mm.
*Apex*.—Rounded to broad acute.
*Shape of petal*.—Ovate.
*Petal margin*.—Entire.
*Petal base*.—Obtuse.
*Petal number*.—4 to 5.
*Petal texture*.—Smooth, glabrous, upper and under side.
*Color*.—Upper surface at first opening: Near RHS White 155A. Upper surface at maturity: Near RHS Red-Purple 63C, flushed 61B. Base White 155A. Under surface at first opening: Near RHS White 155A. Under surface at maturity: Near RHS Red-Purple 63D, flushed 61B. Base White 155A. Upper surface fading to: When completely dry but persistent, fading to near Greyed-Yellow 162A. Lower surface fading to: When completely dry but persistent, fading to near Greyed-Yellow 162A.

Sterile flower pedicel:
*Length*.—1 cm.
*Diameter*.—2 mm.
*Angle*.—0-45°.
*Strength*.—Moderate.
*Texture*.—Glabrous.
*Color*.—Near RHS Yellow-green 145D flushed Greyed-Red 182C.

Peduncle:
*Length*.—Average range 4 to 6 cm.
*Diameter*.—4 mm.
*Angle*.—Upright.
*Strength*.—Moderate.
*Texture*.—Glabrous.
*Color*.—Near RHS Greyed-Red 181C.

Fertile flowers: Not observed.

REPRODUCTIVE ORGANS

Not observed.

OTHER CHARACTERISTICS

Disease resistance: Neither resistance nor susceptibility to diseases or pests has been observed in this variety.
Cold tolerance: −12° C. to 36° C.
Fruit/seed production: Not observed.

What is claimed is:

1. A new and distinct cultivar of *Hydrangea* plant named 'RENSAM' as herein illustrated and described.

* * * * *